(12) United States Patent
Shimizu et al.

(10) Patent No.: US 7,687,633 B2
(45) Date of Patent: Mar. 30, 2010

(54) FILTERS FOR ELECTRONIC DISPLAY DEVICES

(75) Inventors: Ikuo Shimizu, Tokyo (JP); Motoharu Kinugasa, Minoh (JP); Katsumi Ukai, Yokkaichi (JP)

(73) Assignee: Kyowa Hakko Chemical Co., Ltd., Tokyo (JP)

( * ) Notice: Subject to any disclaimer, the term of this patent is extended or adjusted under 35 U.S.C. 154(b) by 410 days.

(21) Appl. No.: 10/579,820

(22) PCT Filed: Dec. 17, 2004

(86) PCT No.: PCT/JP2004/019474

§ 371 (c)(1),
(2), (4) Date: May 17, 2006

(87) PCT Pub. No.: WO2005/059608

PCT Pub. Date: Jun. 30, 2005

(65) Prior Publication Data

US 2007/0105988 A1    May 10, 2007

(30) Foreign Application Priority Data

Dec. 18, 2003   (JP)  ............... 2003-420885

(51) Int. Cl.
*C07C 211/36* (2006.01)
*G02B 5/20* (2006.01)
*H01B 1/12* (2006.01)

(52) U.S. Cl. .............. 546/307; 359/885; 252/589

(58) Field of Classification Search .......... 564/307; 359/885; 252/589
See application file for complete search history.

(56) References Cited

U.S. PATENT DOCUMENTS

| 6,599,605 | B2 * | 7/2003 | Shimizu et al. | ............ | 428/64.1 |
| 2001/0044001 | A1 | 11/2001 | Noguchi et al. | ............ | 428/64.3 |
| 2003/0082329 | A1 | 5/2003 | Shimizu et al. | ............ | 428/64.4 |
| 2003/0157291 | A1 | 8/2003 | Noguchi et al. | ............ | 428/64.4 |

FOREIGN PATENT DOCUMENTS

| JP | 2000-345059 | | 12/2000 |
| JP | 2002-097383 | | 4/2002 |
| WO | WO 01/44375 | * | 6/2001 |

OTHER PUBLICATIONS

Bloor (Can. J. Chem., v. 39 (1961), p. 2256-2261).*
Davis et al. (Int. J. Quant. Chem., v. 72: p. 463-471, 1999).*

* cited by examiner

*Primary Examiner*—Rebecca L Anderson
*Assistant Examiner*—Robert Havlin
(74) *Attorney, Agent, or Firm*—Fitzpatrick, Cella, Harper & Scinto

(57) ABSTRACT

The present invention provides a filter for electronic display devices, comprising a squarylium compound represented by General Formula (I):

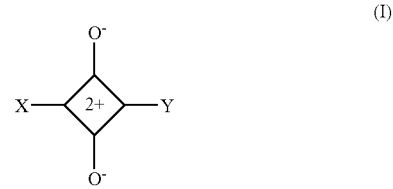

(I)

[wherein X represents a group represented by following Formula (A):

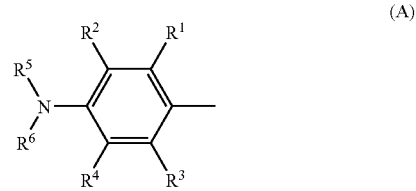

(A)

(wherein $R^1$, $R^2$, $R^3$, and $R^4$ may be the same or different and each represents a hydrogen atom, a halogen atom and the like; and $R^5$ and $R^6$ may be the same or different and each represent a hydrogen atom, an alkyl group optionally having substituent(s) and the like) and the like; and Y represents a group represented by following Formula (C):

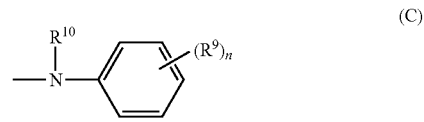

(C)

(wherein $R^9$ represents a halogen atom, an alkyl group optionally having substituent(s) and the like; and $R^{10}$ represents a hydrogen atom, an alkyl group optionally having substituent(s) and the like) and the like, and "n" represents an integer of 0 to 5].

4 Claims, No Drawings

FILTERS FOR ELECTRONIC DISPLAY DEVICES

TECHNICAL FIELD

The present invention relates to filters for electronic display devices.

BACKGROUND ART

Electronic display devices display color images, ideally, by a combination of three primary colors: red, blue, and green. To display images with clearer colors, it has been devised to equip the devices with filters having a color compensating function.

Squarylium compounds have been known as coloring compounds for filters having a color compensating function (refer to Published Japanese Unexamined Patent Application No. 345059/2000). A specific squarylium compound has been known as a colorant for an electronic display device filter that can selectively shield the light having a wavelength of about 480 to about 520 nm (refer to Published Japanese Unexamined Patent Application No. 97383/2002).

DISCLOSURE OF INVENTION

The present invention provides the following (1) to (11):
(1) A filter for electronic display devices, comprising a squarylium compound represented by General Formula (I):

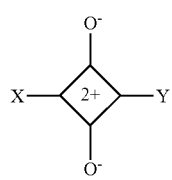

[wherein X represents a group represented by following Formula (A):

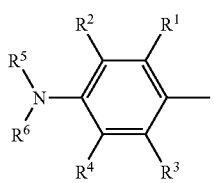

(wherein $R^1$, $R^2$, $R^3$, and $R^4$ may be the same or different and each represents a hydrogen atom, a halogen atom, an alkyl group optionally having substituent(s), an alkoxy group optionally having substituent(s), an aralkyl group optionally having substituent(s), an aryl group optionally having substituent(s), a nitro group, a cyano group, a hydroxyl group, or a heterocyclic group optionally having substituent(s), wherein $R^1$ and $R^2$, or $R^3$ and $R^4$ may be combined together with adjacent two carbon atoms to form a hydrocarbon ring optionally having substituent(s) or a heterocyclic ring optionally having substituent(s); and $R^5$ and $R^6$ may be the same or different and each represents a hydrogen atom, an alkyl group optionally having substituent(s), an aralkyl group optionally having substituent(s), an aryl group optionally having substituent(s), or a heterocyclic group optionally having substituent(s), wherein $R^5$ and $R^6$ may be combined together with the adjacent nitrogen atom to form a heterocyclic ring optionally having substituent(s), or $R^2$ and $R^5$, or $R^4$ and $R^6$ may be combined together with the adjacent N—C—C to form a heterocyclic ring optionally having substituent(s)), or a group represented by following Formula (B):

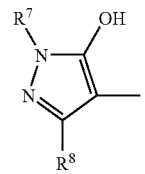

(wherein $R^7$ and $R^8$ may be the same or different and each represents a hydrogen atom, an alkyl group optionally having substituent(s), an aralkyl group optionally having substituent(s), an aryl group optionally having substituent(s), or a heterocyclic group optionally having substituent(s)); and Y represents a group represented by following Formula (C):

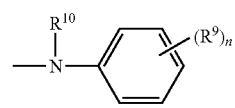

(wherein $R^9$ represents a halogen atom, an alkyl group optionally having substituent(s), an alkoxy group optionally having substituent(s), an aralkyl group optionally having substituent(s), an aryl group optionally having substituent(s), a nitro group, a cyano group, a hydroxyl group, an amino group optionally having substituent(s), —N=N—$R^{9A}$ (wherein $R^{9A}$ represents an alkyl group optionally having substituent(s), an aryl group optionally having substituent(s), or a heterocyclic group optionally having substituent(s)), or a heterocyclic group optionally having substituent(s); "n" represents an integer of 0 to 5, wherein, when "n" is 2 to 5, respective $R^9$s may be the same or different, or further adjacent two $R^9$s may be combined together with the adjacent two carbon atoms to form a hydrocarbon ring optionally having substituent(s) or a heterocyclic ring optionally having substituent(s); and $R^{10}$ represents a hydrogen atom, an alkyl group optionally having substituent(s), an aralkyl group optionally having substituent(s), an aryl group optionally having substituent(s), or a heterocyclic group optionally having substituent(s)), or a group represented by following Formula (D):

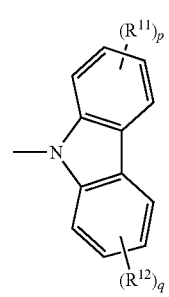

(wherein $R^{11}$ and $R^{12}$ may be the same or different and each represents a halogen atom, an alkyl group optionally having substituent(s), an alkoxy group optionally having substituent(s), an aralkyl group optionally having substituent(s), an aryl group optionally having substituent(s), a nitro group, a cyano group, a hydroxyl group, an amino group optionally having substituent(s), or a heterocyclic group optionally having substituent(s); and "p" and "q" may be the same or different and each represents an integer of 0 to 4, wherein, when "p" or "q" is 2 to 4, respective $R^{11}$s and respective $R^{12}$s may be the same or different)].

(2) A filter for electronic display devices, comprising a squarylium compound represented by General Formula (Ia):

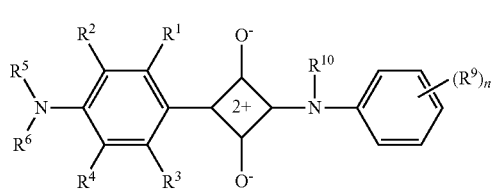

(wherein $R^1$, $R^2$, $R^3$, $R^4$, $R^5$, $R^6$, $R^9$, $R^{10}$, and "n" are as defined above, respectively).

(3) The filter for electronic display devices according to (2), wherein $R^1$, $R^2$, $R^3$, and $R^4$ may be the same or different and are each a hydrogen atom, an alkyl group, or a hydroxyl group; $R^5$ and $R^6$ may be the same or different and are each an alkyl group; $R^9$ is an alkyl group or an alkoxy group; $R^{10}$ is a hydrogen atom or an alkyl group; and "n" is an integer of 0 to 2.

(4) A filter for electronic-display devices, comprising a squarylium compound represented by General Formula (Ib):

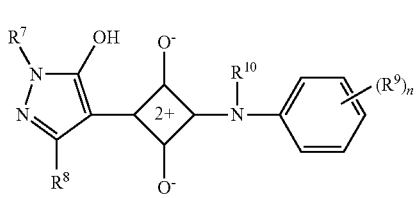

(wherein $R^7$, $R^8$, $R^9$, $R^{10}$, and "n" are as defined above, respectively).

(5) The filter for electronic display devices according to (4), wherein $R^7$ and $R^8$ may be the same or different and are an alkyl group or an aryl group; $R^9$ is an alkoxyl group, an amino group having substituent(s), or —N=N—$R^{9A}$ (wherein $R^{9A}$ is as defined above); $R^{10}$ is a hydrogen atom; and "n" is an integer of 0 to 2.

(6) A filter for electronic display devices, comprising a squarylium compound represented by General Formula (Ic):

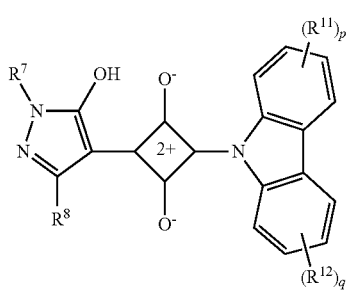

(wherein $R^7$, $R^8$, $R^{11}$, $R^{12}$, "p", and "q" are as defined above, respectively).

(7) The filter for electronic display devices according to (6), wherein $R^7$ and $R^8$ may be the same or different and are each an alkyl group; and "p" and "q" are 0.

(8) A squarylium compound represented by General Formula (Ib):

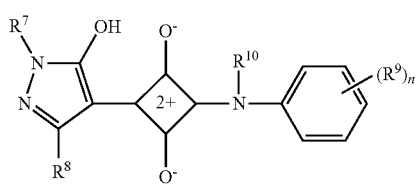

(wherein $R^7$, $R^8$, $R^9$, $R^{10}$, and "n" are as defined above, respectively).

(9) The squarylium compound according to (8), wherein $R^7$ and $R^8$ may be the same or different and are each an alkyl group or an aryl group; $R^9$ is an alkoxy group, an amino group having substituent(s), or —N=N—$R^{9A}$ (wherein $R^{9A}$ is as defined above); $R^{10}$ is a hydrogen atom; and "n" is an integer of 0 to 2.

(10) A squarylium compound represented by General Formula (Ic):

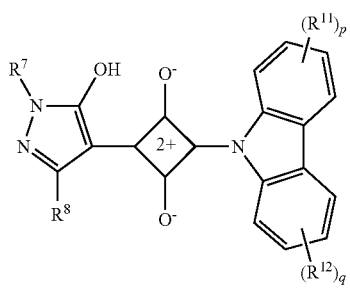

(wherein $R^7$, $R^8$, $R^{11}$, $R^{12}$, "p", and "q" are as defined above, respectively).

(11) The squarylium compound according to (10), wherein $R^7$ and $R^8$ may be the same or different and are each an alkyl group; and "p" and "q" are 0.

Hereinafter, the compound represented by General Formula (I) is referred to as compound (I). Compounds with other formula numbers are also expressed in the same manner.

In the definition of each group in the general formulae, examples of the alkyl group and an alkyl moiety in the alkoxy group include linear or branched alkyl groups having one to six carbon atoms and cyclic alkyl groups having three to eight carbon atoms, specifically, such as methyl group, ethyl group, propyl group, isopropyl group, butyl group, isobutyl group, sec-butyl group, tert-butyl group, pentyl group, isopentyl group, 2-methylbutyl group, tert-pentyl group, hexyl group, cyclopropyl group, cyclobutyl group, cyclopentyl group, cyclohexyl group, cycloheptyl group, and cyclooctyl group.

Examples of the aralkyl group include aralkyl groups having seven to fifteen carbon atoms, specifically, such as benzyl group, phenethyl group, phenylpropyl group, and naphthylmethyl group.

Examples of the aryl group include phenyl group, naphthyl group, and anthryl group.

The halogen atom includes fluorine atom, chlorine atom, bromine atom, and iodine atom.

Examples of a heterocyclic ring in the heterocyclic group include heteroaromatic rings (aromatic heterocyclic rings) and alicyclic heterocyclic rings.

Examples of the heteroaromatic rings include 5- or 6-membered monocyclic heteroaromatic rings containing at least one-atom selected from nitrogen atoms, oxygen atoms, and sulfur atoms; and fused bicyclic or tricyclic heteroaromatic groups containing at least one atom selected from nitrogen atoms, oxygen atoms, and sulfur atoms wherein 3- to 8-membered rings are fused. More specific examples thereof are pyridine ring, pyrazine ring, pyrimidine ring, pyridazine ring, quinoline ring, isoquinoline ring, phthalazine ring, quinazoline ring, quinoxaline ring, naphthyridine ring, cinnoline ring, pyrrole ring, pyrazole ring, imidazole ring, triazole ring, tetrazole ring, thiophene ring, furan ring, thiazole ring, oxazole ring, indole ring, isoindole ring, indazole ring, benzimidazole ring, benzotriazole ring, benzothiazole ring, benzoxazole ring, purine ring, carbazole ring, and the like.

Examples of the alicyclic heterocyclic rings include 5- to 6-membered monocyclic alicyclic heterocyclic rings containing at least one atom selected from nitrogen atoms, oxygen atoms and sulfur atoms; and fused bicyclic or tricyclic alicyclic heterocyclic rings coming at least one atom selected from nitrogen atoms, oxygen atoms and sulfur atoms wherein 3- to 8-membered rings are fused. More specific examples thereof are pyrrolidine ring, piperidine ring, piperazine ring, morpholine ring, thiomorpholine ring, homopiperidine ring, homopiperazine ring, tetrahydropyridine ring, tetrahydroquinoline ring, tetrahydroisoquinoline ring, tetrahydrofuran ring, tetrahydropyran ring, dihydrobenzofuran ring, tetrahydrocarbazole ring, and the like.

Examples of the hydrocarbon ring formed by $R^1$ and $R^2$, or $R^3$ and $R^4$ taken together with the adjacent two carbon atoms, and of the hydrocarbon ring formed by taking adjacent two $R^9$s together with the adjacent two carbon atoms include unsaturated hydrocarbon rings having five to ten carbon atoms, such as cyclopentene ring, cyclohexene ring, cycloheptene ring, cyclooctene ring, benzene ring, and naphthalene ring.

Examples of the heterocyclic ring formed by $R^1$ and $R^2$, or $R^3$ and $R^4$ together with the adjacent two carbon atoms, and of the heterocyclic ring formed by adjacent two $R^9$s together with the adjacent two carbon atoms include the above-mentioned heteroaromatic rings.

Examples of the heterocyclic ring formed by $R^2$ and $R^5$, or $R^4$ and $R^6$ together with the adjacent N—C—C, and of the heterocyclic ring formed by $R^5$ and $R^6$ together with the adjacent nitrogen atom include 5- or 6-membered monocyclic heterocyclic rings containing at least one nitrogen atom, (wherein the monocyclic heterocyclic rings may further contain another nitrogen atom, an oxygen atom, or a sulfur atom); and fused bicyclic or tricyclic heterocyclic rings containing at least one nitrogen atom, wherein 3- to 8-membered rings are fused. (The fused heterocyclic rings may further contain another nitrogen atom, an oxygen atom, or a sulfur atom.) More specific examples thereof are pyrrolidine ring, piperidine ring, piperazine ring, morpholine ring, thiomorpholine ring, homopiperidine ring, homopiperazine ring, tetrahydropyridine ring, tetrahydroquinoline ring, tetrahydroisoquinoline ring, pyrrole ring, imidazole ring, pyrazole ring, indole ring, indoline ring, and isoindole ring and the like. However, the heterocyclic ring formed by $R^2$ and $R^5$, or $R^4$ and $R^6$ together with the adjacent N—C—C contains at least one or more carbon-carbon double bond(s) in the ring.

Substituents of the alkyl group and the alkoxy group may each have, for example, one to three substituents which may be the same or different. Specific examples of the substituents include hydroxyl group, carboxyl group, halogen atom, alkoxy group, alkoxyalkoxy group and the like. The halogen atom and the alkoxy group are as defined above, respectively. The two alkoxy moieties of the alkoxyalkoxy group are as defined above, respectively.

The aralkyl group, the aryl group, the heterocyclic group, the hydrocarbon ring formed by $R^1$ and $R^2$, or $R^3$ and $R^4$ together with the adjacent two carbon atoms, the hydrocarbon ring formed by adjacent two $R^9$s together with the adjacent two carbon atoms, the heterocyclic ring formed by $R^1$ and $R^2$, or $R^3$ and $R^4$ together with the adjacent two carbon atoms, the heterocyclic ring formed by $R^2$ and $R^5$, or $R^4$ and $R^6$ together with the adjacent N—C—C, the heterocyclic ring formed by $R^5$ and $R^6$ together with the adjacent nitrogen atom, and the heterocyclic ring formed by adjacent two $R^9$s together with the adjacent two carbon atoms may each have, for example, one to five substituents which may be the same or different. Specific examples of the substituents are hydroxyl group, carboxyl group, halogen atom, alkyl group, alkoxy group, nitro group, and amino group optionally having substituent(s), and the like. (Examples of substituents of the amino group are as mentioned below.) The halogen atoms, the alkyl groups, and the alkoxy groups are as defined above, respectively.

Examples of substituents of the amino group include one or two substituents which may be the same or different, such as alkyl group, aralkyl group, and aryl group. The alkyl group, the aralkyl group, and the aryl group are as defined above, respectively.

Compounds (I) can be prepared according to a known procedure (e.g., PCT International Publications No. WO 01/44233 and No. WO 01/44375).

For example, a compound (Ib) and a compound (Ic) can be prepared in the following manner.

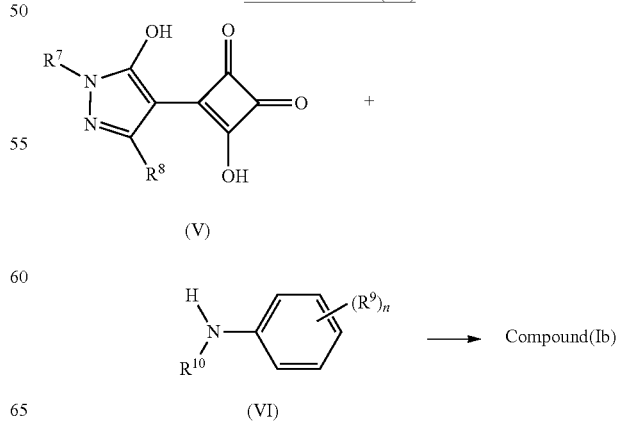

Reaction Scheme (1-a)

Reaction Scheme (1-b)

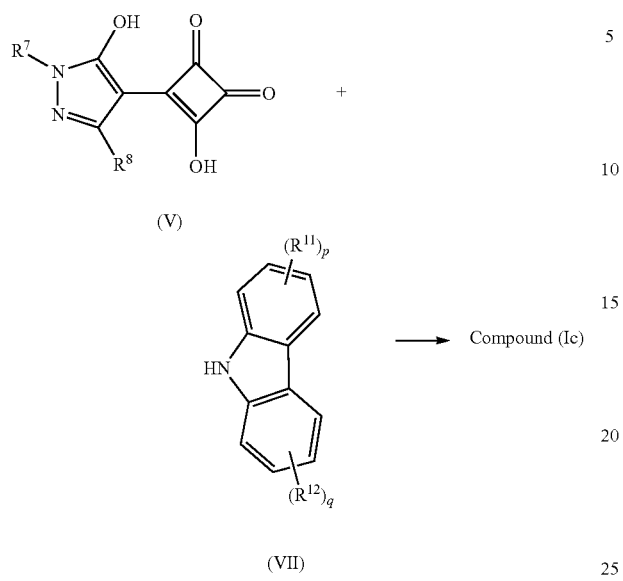

(wherein $R^7$, $R^8$, $R^9$, $R^{10}$, $R^{11}$, $R^{12}$, "n", "p", and "q" are as defined above, respectively).

Reaction Scheme (1-a)

The compound (V) can be prepared in a similar manner to a known method (e.g., PCT International Publications No. WO 01/44233).

The compound (Ib) can be obtained by reacting the compound (V) with 1- to 5-fold moles of the compound (VI) at 80° C. to 120° C. for one to fifteen hours in a solvent.

Examples of the solvent include an alcohol solvent such as ethanol, propanol, isopropyl alcohol, butanol, or octanol; and a mixed solvent of the alcohol solvent with benzene, toluene, or xylene, which the mixed solvent contains 50 percent by volume or more of the alcohol solvent.

After the reaction, if necessary, the target compound may be purified by a procedure generally used in synthetic organic chemistry, such as column chromatography, recrystallization, or washing with a solvent.

Reaction Scheme (1-b)

The compound (Ic) can be prepared by reacting the compound (V) and 1- to 5-fold moles of the compound (VII) at a temperature of 80° C. to 120° C. for one to fifteen hours in a solvent.

Examples of the solvent include an alcohol solvent such as ethanol, propanol, isopropyl alcohol, butanol, or octanol; and a mixed solvent of the alcohol solvent with benzene, toluene, or xylene, which the mixed solvent contains 50 percent by volume or more of the alcohol solvent.

After the reaction, if necessary, the target compound may be purified by a procedure generally used in synthetic organic chemistry, such as column chromatography, recrystallization, or washing with a solvent.

Preferred examples of the compound (I) are illustrated below. In the structural formulae of Compounds 1 to 17, Me represents a methyl group; Et represents an ethyl group; Pr represents a n-propyl group; and Bu represents a n-butyl group.

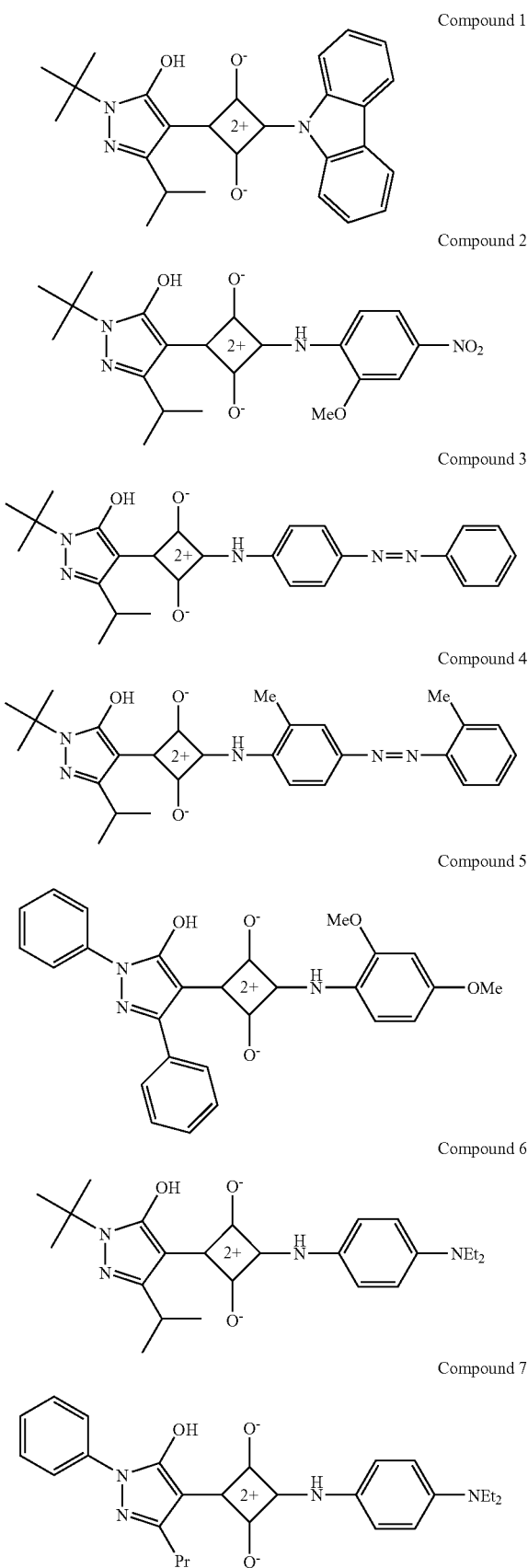

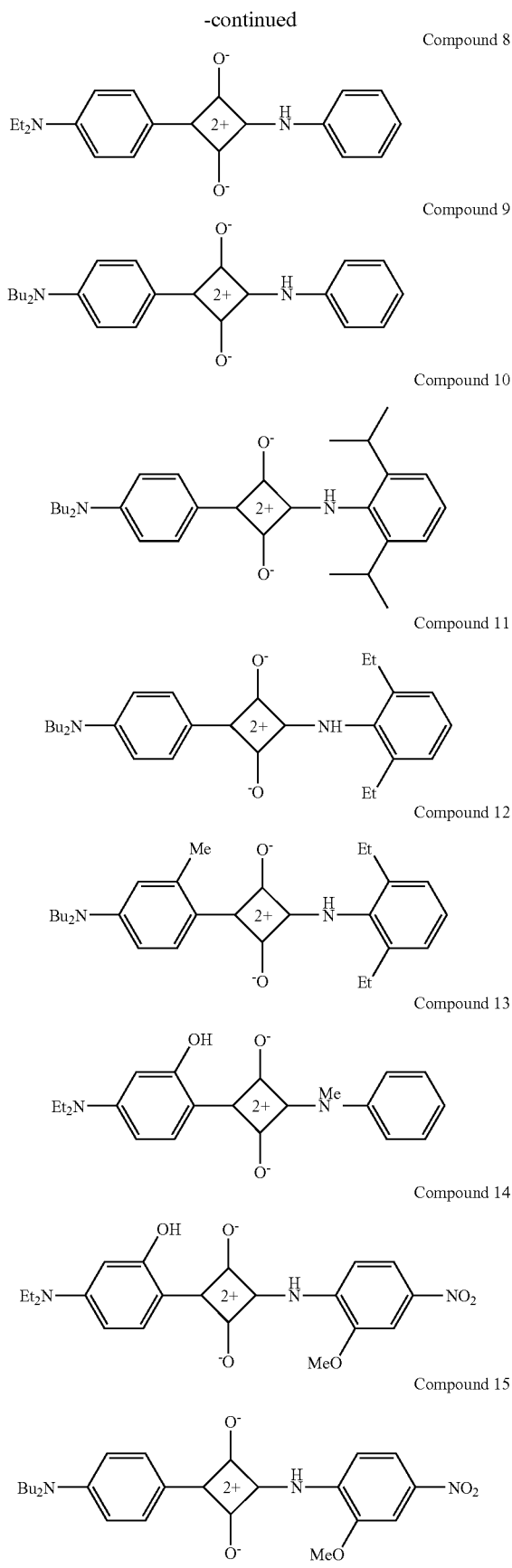

Next, the filter for electronic display devices of the present invention will be illustrated.

Examples of the electronic display devices include liquid crystal displays, plasma displays, and organic electroluminescence displays and the like. Among them, plasma displays and the like are preferred.

The compound (I) used for in the filter for electronic display devices of the present invention preferably has an absorption maximum in an absorption region of 450 nm to 570 nm in a chloroform solvent. The compound (I) also preferably has logarithm of a molar extinction coefficient of 4.5 or more, and more preferably 4.8 or more. Since the compound (I) has such a high molar extinction coefficient, the filter for electronic display devices of the present invention can exhibit sufficient performance even when only a small amount of the compound (I) is used therein.

The filter for electronic display devices of the present invention preferably has an absorption maximum in an absorption region of 450 to 570 nm.

The filter for electronic display devices of the present invention is preferably produced by applying a coating composition containing the compound (I) to an optically transparent substrate, and evaporating an organic solvent. If necessary, another optically transparent substrate may be laminated.

The coating composition may be prepared by dissolving a solution of an organic solvent containing the compound (I) with a binder in the organic solvent.

Examples of the organic solvent include ethers such as dimethoxyethane, methoxyethoxyethane, tetrahydrofuran, and dioxane; ketones such as acetone, methyl ethyl ketone, methyl isobutyl ketone, and cyclohexanone; and aromatic hydrocarbons such as benzene, toluene, xylene, and monochlorobenzene. These organic solvents are preferably used in an amount 10 to 3000-fold by weight to the compound (I).

Examples of the binder include polyester resin, polycarbonate resin, polyacrylic acid resin, polystyrenic resin, poly(vinyl chloride) resin, poly(vinyl acetate) resin and the like. The binder is preferably used in an amount 10- to 500-fold by weight to the compound (I).

The optically transparent substrate is not specifically limited, as long as it comprises an optically transparent resin or glass having low absorption and scattering. Examples of the resin include polyester resin, polycarbonate resin, poly(acrylic acid) resin, polystyrenic resin, poly(vinyl chloride) resin, poly(vinyl acetate) resin and the like.

The coating composition containing the compound (I) can be applied to the optically transparent substrate according to a known coating procedure, such as bar coating, spraying, roll coating, or dipping (e.g., U.S. Pat. No. 2,681,294).

The compounds (I) have a high solubility in an organic solvent and are suitable for a method of preparing a filter for electronic display devices using the above coating composition.

The filter for electronic display devices of the present invention may also be prepared by directly dissolving or dispersing the compound (I) in a resin constituting an optically transparent substrate, forming the solution or dispersion into a film, and, if necessary, laminating the film with other optically transparent substrates at one or both sides thereof.

The film formed from the compound (I) preferably has an absorption width of 50% transmittance near an absorption maximum wavelength of 80 nm or less. The absorption width herein is a difference between the maximum and minimum absorption wavelengths which show 50% or less of transmittance near the absorption maximum wavelength. The film containing the compound (I) also preferably has a sufficient transmittance in a region of 500 to 600 nm. For example, in the case of the compound (I) having an absorption maximum in a region of 450 to 570 nm, the resulting film preferably has a transmittance of 80% or more at 600 nm, and more preferably 90% or more.

The filter for electronic display devices according to the present invention can selectively shield the light having such a wavelength that reduces the color purity while maintaining the brightness in visible field, and is excellent in the color correcting function. Therefore, the filter can provide clear images excellent in colors.

The filter for electronic display devices of the present invention can be used for, for example, cathode-ray tubes, fluorescent display tubes, electroluminescence panels, light emitting diodes, plasma display panels, incandescent lamps, laser displays, liquid crystal displays, electrochromic displays and the like.

In particular, the filter for electronic display devices of the present invention can control the emission intensity of green phosphors having a high luminance efficacy.

The present invention will be illustrated in further detail with reference to the following Examples, Reference Examples, and Test Example.

BEST MODE FOR CARRYING OUT THE INVENTION

Example 1

Preparation of Compound 1

Starting material 3-hydroxy-4-(1-tert-butyl-5-hydroxy-3-isopropylpyrazol-4-yl)cyclobutene-1,2-dione was synthesized according to the method described in PCT International Publication No. WO 01/44233.

To a mixed solvent of 20 ml of butanol and 20 ml of toluene, 2.00 g of 3-hydroxy-4-(1-tert-butyl-5-hydroxy-3-isopropylpyrazol-4-yl)cyclobutene-1,2-dione and 1.60 g of carbazole were added, and the mixture was reacted at 100° C. to 110° C. for twelve hours. The reaction mixture was then cooled to 20° C. to 30° C., and the precipitated solid was collected by filtration. To 1.19 g of the collected solid 70 ml of methanol was added, followed by stirring at 75° C. for one hour. The mixture was cooled to 20° C. to 30° C., and the orange precipitate was collected by filtration to thereby yield Compound 1 (0.49 g).

$^1$H-NMR δ (CDCl$_3$) ppm: 1.32 (6H, d, J=6.8 Hz), 1.64 (9H, s), 3.64 (1H, m), 7.38 (2H, td, J=7.6 Hz, 1.2 Hz), 7.47 (2H, td, J=7.6 Hz, 1.2 Hz), 7.89 (1H, dd, J=7.6 Hz, 0.8 Hz), 8.92 (1H, d, J=8.4 Hz).

Example 2

Preparation of Compound 2

To a mixed solvent of 20 ml of butanol and 20 ml of toluene, 1.50 g of 3-hydroxy-4-(1-tert-butyl-5-hydroxy-3-isopropylpyrazol-4-yl)cyclobutene-1,2-dione and 1.18 g of 2-methoxy-4-nitroaniline were added and the mixture was reacted at 100° C. to 110° C. for five hours. The reaction mixture was then cooled to 20° C. to 30° C., and the orange precipitate was collected by filtration to thereby yield Compound 2 (1.27 g).

$^1$H-NMR δ (CDCl$_3$) ppm: 1.27 (6H, d, J=6.8 Hz), 1.59 (9H, s), 3.51 (1H, m), 4.05 (3H, s), 7.79 (1H, d, J=2.4 Hz), 7.97 (1H, dd, J=8.8 Hz, 2.4 Hz), 8.53 (1H, brs).

Example 3

Preparation of Compound 3

To a mixed solvent of 20 ml of butanol and 20 ml of toluene, 2.00 g of 3-hydroxy-4-(1-tert-butyl-5-hydroxy-3-isopropylpyrazol-4-yl)cyclobutene-1,2-dione and 1.70 g of p-aminoazobenzene were added and the mixture was reacted at 100° C. to 110° C. for five hours. The reaction mixture was then cooled to 20° C. to 30° C., and the orange precipitate was collected by filtration to thereby yield Compound 3 (2.46 g).

Example 4

Preparation of Compound 4

To a mixed solvent of 10 ml of butanol and 10 ml of toluene, 1.0 g of 3-hydroxy-4-(1-tert-butyl-5-hydroxy-3-isopropylpyrazol-4-yl)cyclobutene-1,2-dione and 1.05 g of 4'-amino-2,3'-dimethylazobenzene were added and the mixture was reacted at 100° C. to 110° C. for 2.5 hours. The reaction mixture was then cooled to 20° C. to 30° C., and the orange precipitate was collected by filtration to thereby yield Compound 4 (1.26 g).

Example 5

Preparation of Compound 5

Starting material 3-hydroxy-4-(5-hydroxy-1,3-diphenylpyrazol-4-yl)cyclobutene-1,2-dione was synthesized in a similar manner to the method described in PCT International Publication No. WO 01/44233.

To a mixed solvent of 10 ml of butanol and 10 ml of toluene, 1.00 g of 3-hydroxy-4-(5-hydroxy-1,3-diphenylpyrazol-4-yl)cyclobutene-1,2-dione and 0.65 g of 2,4-dimethoxyaniline were added and the mixture was reacted at 100° C. to 110° C. for 3.5 hours. The reaction mixture was then cooled to 20° C. to 30° C., and the orange precipitate was collected by filtration to thereby yield Compound 5 (1.45 g).

Example 6

Preparation of Compound 6

Starting material 3-hydroxy-4-(1-tert-butyl-5-hydroxy-3-isopropylpyrazol-4-yl)cyclobutene-1,2-dione was synthesized in a similar manner to the method described in PCT International Publication No. WO 01/44233.

To a mixed solvent of 4 ml of butanol and 4 ml of toluene, 0.36 g of 3-hydroxy-4-(1-tert-butyl-5-hydroxy-3-isopropylpyrazol-4-yl)cyclobutene-1,2-dione and 0.38 g of N,N-diethyl-1,4-phenylenediamine were added, and the mixture was reacted at 100° C. to 110° C. for five hours. The reaction mixture was then cooled to 20° C. to 30° C., and the orange precipitate was collected by filtration to thereby yield Compound 6 (0.26 g).

$^1$H-NMR δ (CDCl$_3$) ppm: 1.18 (6H, t, J=7.2 Hz), 1.30 (6H, d, J=6.8 Hz), 1.59 (9H, s), 3.38 (4H, q, J=7.2 Hz), 3.69 (1H, m), 6.67 (2H, d, J=9.6 Hz), 7.77 (2H, d, J=9.6 Hz), 11.64 (1H, brs), 13.73 (1H, brs).

Example 7

Preparation of Compound 7

Starting material 3-hydroxy-4-(5-hydroxy-1-phenyl-3-propylpyrazol-4-yl)cyclobutene-1,2-dione was synthesized in a similar manner to the method described in PCT International Publication No. WO 01/44233.

To a mixed solvent of 20 ml of butanol and 20 ml of toluene, 1.50 g of 3-hydroxy-4-(5-hydroxy-1-phenyl-3-propylpyrazol-4-yl)cyclobutene-1,2-dione and 1.16 g of N,N-diethyl-1,4-phenylenediamine were added and the mixture was reacted at 100° C. to 110° C. for 4.5 hours. The reaction mixture was then cooled to 20° C. to 30° C., and the red precipitate was collected by filtration to thereby yield Compound 7 (2.05 g).

$^1$H-NMR δ (CDCl$_3$) ppm: 0.96 (3H, t, J=7.2 Hz), 1.09 (6H, t, J=6.8 Hz), 1.67 (2H, m), 2.83 (2H, t, J=7.6 Hz), 3.37 (4H, q, J=6.8 Hz), 6.71 (2H, d, J=9.2 Hz), 7.32 (1H, t, J=7.6 Hz), 7.49 (2H, t, J=8.0 Hz), 7.64 (2H, d, J=12.8 Hz), 7.76 (2H, d, J=7.6 Hz), 12.68 (1H, brs).

Reference Example 1

Preparation of Compound 8

Starting material 3-hydroxy-4-[4-(N,N-diethylamino)phenyl]cyclobutene-1,2-dione was synthesized in a similar manner to the method described in PCT International Publication No. WO 01/44375.

To a mixed solvent of 20 ml of butanol and 10 ml of toluene, 1.18 g of 3-hydroxy-4-[4-(N,N-diethylamino)phenyl]cyclobutene-1,2-dione and 0.68 g of aniline were added and the mixture was reacted at 100° C. to 110° C. for 4.0 hours. The reaction mixture was then cooled to 20° C. to 30° C., and the reddish purple precipitate was collected by filtration to thereby yield Compound 8 (1.45 g).

$^1$H-NMR δ (CDCl$_3$) ppm: 1.15 (6H, t, J=7.2 Hz), 3.48 (4H, q, J=7.2 Hz), 6.84 (2H, d, J=9.2 Hz), 7.27 (1H, t, J=7.2 Hz), 7.46 (2H, t, J=8.0 Hz), 7.95 (2H, dd, J=8.4 Hz and 1.2 Hz), 8.04 (2H, d, J=9.2 Hz).

Reference Example 2

Preparation of Compound 9

Starting material 3-hydroxy-4-[4-(N,N-diethylamino)phenyl]cyclobutene-1,2-dione was synthesized in a similar manner to the method described in PCT International Publication No. WO 01/44375.

To a mixed solvent of 2 ml of butanol and 1 ml of toluene, 0.18 g of 3-hydroxy-4-[4-(N,N-diethylamino)phenyl]cyclobutene-1,2-dione and 0.07 g of aniline were added and the mixture was reacted at 100° C. to 110° C. for 2.0 hours. The reaction mixture was then cooled to 20° C. to 30° C., and the red precipitate was collected by filtration to thereby yield Compound 9 (0.15 g).

$^1$H-NMR δ (CDCl$_3$) ppm: 0.99 (6H, t, J=7.6 Hz), 1.40 (4H, m), 1.64 (4H, m), 3.39 (4H, t, J=7.6 Hz), 6.71 (2H, d, J=9.2 Hz), 7.25 (1H, t, J=7.2 Hz), 7.46 (2H, t, J=7.2 Hz), 8.20 (2H, d, J=7.6 Hz), 8.26 (2H, d, J=9.2 Hz).

Reference Example 3

Preparation of Compound 10

To a mixed solvent of 5 ml of butanol and 2.5 ml of toluene 0.30 g of 3-hydroxy-4-[4-(N,N-diethylamino)phenyl]cyclobutene-1,2-dione and 0.26 g of 2,6-diisopropylaniline were added, and the mixture was reacted at 100° C. to 110° C. for 1.5 hours. The reaction mixture was concentrated, added with 5 ml of methanol, and stirred at 65° C. for 30 minutes. After cooling to 0° C. to 5° C., the orange precipitate was collected by filtration to thereby yield Compound 10 (0.19 g).

$^1$H-NMR δ (CDCl$_3$) ppm: 0.94 (6H, t, J=7.6 Hz), 1.25 (12H, d, J=6.8 Hz), 1.34 (4H, m), 1.57 (4H, m), 3.23 (2H, m), 3.32 (4H, t, J=7.6 Hz), 6.57 (2H, d, J=9.6 Hz), 7.25 (2H, d, J=5.6 Hz), 7.40 (1H, t, J=7.6 Hz), 8.03 (2H, d, J=9.6 Hz).

Reference Example 4

Preparation of Compound 11

To a mixed solvent of 4 ml of butanol and 2 ml of toluene, 0.28 g of 3-hydroxy-4-[4-(N,N-diethylamino)phenyl]cyclobutene-1,2-dione and 0.18 g of 2,6-diethylaniline were added and the mixture was reacted at 100° C. to 110° C. for 1.5 hours. The reaction mixture was concentrated, added with 5 ml of methanol, and stirred at 65° C. for 30 minutes. After cooling to 0° C. to 5° C., the orange precipitate was collected by filtration to thereby yield Compound 11 (0.17 g).

$^1$H-NMR δ (CDCl$_3$) ppm: 0.95 (6H, t, J=7.6 Hz), 1.24 (6H, t, J=7.6 Hz), 1.35 (4H, m), 1.57 (4H, m), 2.76 (4H, q, J=7.6 Hz), 3.33 (4H, t, J=7.6 Hz), 6.59 (2H, d, J=8.8 Hz), 7.20 (2H, d, J=8.0 Hz), 7.32 (1H, dd, J=8.0 Hz, 7.2 Hz), 8.05 (2H, d, J=8.8 Hz).

Reference Example 5

Preparation of Compound 12

Starting material 3-hydroxy-4-[4-(N,N-dibutylamino)-3-methylphenyl]cyclobutene-1,2-dione was synthesized in a similar manner to the method described in PCT International Publication No. WO 01/44375.

To a mixed solvent of 4 ml of butanol and 2 ml of toluene, 0.28 g of 3-hydroxy-4-[4-(N,N-dibutylamino)-3-methylphenyl]cyclobutene-1,2-dione and 0.25 g of 2,6-diethylaniline were added and the mixture was reacted at 100° C. to 110° C. for one hour. The reaction mixture was concentrated, added with 3 ml of methanol, and stirred at 65° C. for 30 minutes. After cooling to 20° C. to 30° C., the orange precipitate was collected by filtration to thereby yield Compound 12 (0.22 g).

$^1$H-NMR δ (CDCl$_3$) ppm: 0.95 (6H, t, J=7.6 Hz), 1.23 (6H, t, J=7.6 Hz), 1.34 (4H, m), 1.56 (4H, m), 2.65 (1H, s), 2.76 (4H, q, J=7.6 Hz), 3.31 (4H, t, J=7.6 Hz), 6.39 (1H, s), 6.41 (1H, dd, J=8.8 Hz, 2.8 Hz), 7.18 (2H, d, J=7.6 Hz), 7.30 (1H, dd, J=8.0 Hz, 6.8 Hz), 8.42 (1H, d, J=8.8 Hz).

Reference Example 6

Preparation of Compound 13

Starting material 3-hydroxy-4-[4-(N,N-diethylamino)-3-hydroxyphenyl]cyclobutene-1,2-dione was synthesized in a similar manner to the method described in PCT International Publication No. WO 01/44375.

To a mixed solvent of 2 ml of butanol and 2 ml of toluene, 0.50 g of 3-hydroxy-4-[4-(N,N-diethylamino)-3-hydroxyphenyl]cyclobutene-1,2-dione and 0.29 g of N-methylaniline were added and the mixture was reacted at 100° C. to 110° C. for five hours. After cooling to 0° C. to 5° C., the orange precipitate was collected by filtration to thereby yield Compound 13 (0.57 g).

Reference Example 7

Preparation of Compound 14

To a mixed solvent of 2 ml of butanol and 2 ml of toluene, 0.50 g of 3-hydroxy-4-[4-(N,N-diethylamino)-3-hydroxyphenyl]cyclobutene-1,2-dione and 0.42 g of 2-methoxy-4-nitroaniline were added and the mixture was reacted at 100° C. to 110° C. for five hours. After cooling to room temperature, the gray precipitate was collected by filtration to thereby yield Compound 14 (0.71 g).

Reference Example 8

Preparation of Compound 15

To a mixed solvent of 2 ml of butanol and 2 ml of toluene, 0.50 g of 3-hydroxy-4-[4-(N,N-diethylamino)-3-hydroxyphenyl]cyclobutene-1,2-dione and 0.36 g of 2-methoxy-4-nitroaniline were added and the mixture was reacted at 100° C. to 110° C. for five hours. After cooling the reaction mixture to room temperature, 2 ml of methanol was added, and the green precipitate was collected by filtration to thereby yield Compound 15 (0.12 g).

Reference Example 9

Preparation of Compound 16

Starting material 3-hydroxy-4-[4-(N,N-dibutylamino)-3-methylphenyl]cyclobutene-1,2-dione was synthesized in a similar manner to the method described in PCT International Publication No. WO 01/44375.

To a mixed solvent of 5 ml of butanol and 2.5 ml of toluene, 0.40 g of 3-hydroxy-4-[4-(N,N-dibutylamino)-3-methylphenyl]cyclobutene-1,2-dione and 0.19 g of 2,4-dimethylaniline were added and the mixture was reacted at 100° C. to 110° C. for 4.5 hours. The reaction mixture was concentrated, added with 3 ml of methanol, and stirred at 75° C. for 10 minutes. After cooling to 0° C. to 5° C., the reddish brown precipitate was collected by filtration to thereby yield Compound 16 (0.39 g).

Reference Example 10

Preparation of Compound 17

To a mixed solvent of 5 ml of butanol and 2.5 ml of toluene, 0.40 g of 3-hydroxy-4-[4-(N,N-dibutylamino)-3-methylphenyl]cyclobutene-1,2-dione and 0.21 g of 2,4,6-trimethylaniline were added and the mixture was reacted at 100° C. to 110° C. for 2.5 hours. After cooling to 0° C. to 5° C., the orange precipitate was collected by filtration to thereby yield Compound 17 (0.22 g).

Test Example 1

The absorption maximum wavelength ($\lambda$max) and logarithm of molar extinction coefficient (log$\epsilon$) of Compounds 1 to 12 were determined (800 to 300 nm) using UV-Vis Spectorophotometer [UV-4000 (Hitachi Co., Ltd.)]. The results are shown in Table 1.

TABLE 1

Spectroscopic property of squarylium compounds

| Compound | Spectroscopic property (Chloroform solution) | |
|---|---|---|
| | $\lambda$max (nm) | log$\epsilon$ |
| 1 | 501.0 | 4.9 |
| 2 | 489.0 | 4.9 |
| 3 | 487.0 | 4.8 |
| 4 | 471.5 | 4.7 |
| 5 | 462.5 | 4.7 |
| 6 | 482.5 | 4.7 |
| 7 | 490.5 | 4.6 |
| 8 | 507.0 | 5.1 |
| 9 | 509.5 | 5.1 |
| 10 | 469.5 | 5.0 |
| 11 | 470.5 | 5.0 |
| 12 | 481.0 | 5.0 |
| 13 | 500.0 | 5.0 |
| 14 | 560.0 | 5.2 |
| 15 | 562.0 | 5.0 |
| 16 | 514.0 | 4.9 |
| 17 | 482.0 | 5.0 |

Example 8

A 1.0 percent by weight solution of Compound 1, 2, 10, 11, or 12 in dimethoxyethane and a 20 percent by weight solution of a polyester resin [Vylon 200 (a product of TOYOBO Co., Ltd.)] in dimethoxyethane were mixed at a ratio of 7:2, and the mixture was applied to a glass substrate using a spin coater, and dried to yield a coating film. The absorption maximum wavelength, the absorption width of 50% transmittance, and the transmittance at 600 nm of the film were determined (800 to 300 nm) using UV-Vis Spectorophotometer [UV-4000 (Hitachi Co., Ltd.)]. The results are shown in Table 2.

TABLE 2

Absorption maximum wavelengths, absorption widths of 50% transmittance, and transmittances at 600 nm of squarylium compounds in a film

| | Absorption maximum wavelength | Absorption width of 50% transmittance | Transmittance at 600 nm |
|---|---|---|---|
| Compound 1 | 505.0 nm | 71.5 nm | 95% or more |
| Compound 2 | 496.0 nm | 76.0 nm | 95% or more |
| Compound 10 | 474.0 nm | 67.5 nm | 95% or more |
| Compound 11 | 475.0 nm | 71.5 nm | 95% or more |
| Compound 12 | 486.0 nm | 70.0 nm | 95% or more |

These results show, for example, that the filters for electronic display devices of the present invention can improve a color in the vicinity of green, can selectively shield the light having such a wavelength as to reduce the color purity, and can provide clear images.

INDUSTRIAL APPLICABILITY

The present invention can provide, for example, filters for electric display devices which improve colors.

The invention claimed is:

1. A filter for electronic display devices, comprising a squarylium compound represented by Formula (Ia):

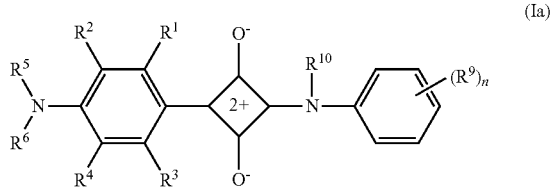

wherein $R^1$, $R^2$, $R^3$, and $R^4$ are independently a hydrogen atom, an alkyl group, or a hydroxyl group;
$R^5$ and $R^6$ are independently an alkyl group;
$R^9$ is an alkyl group or an alkoxy group;
$R^{10}$ is a hydrogen atom or an alkyl group; and
n is an integer of 0 to 2.

2. The filter for electronic display devices according to claim 1, wherein $R^9$ is an alkyl group; and n is an integer of 1 or 2.

3. The filter for electronic display devices according to claim 1, wherein $R^{10}$ is an alkyl group.

4. The filter for electronic display devices according to claim 2, wherein $R^{10}$ is an alkyl group.

* * * * *